Figure 3:
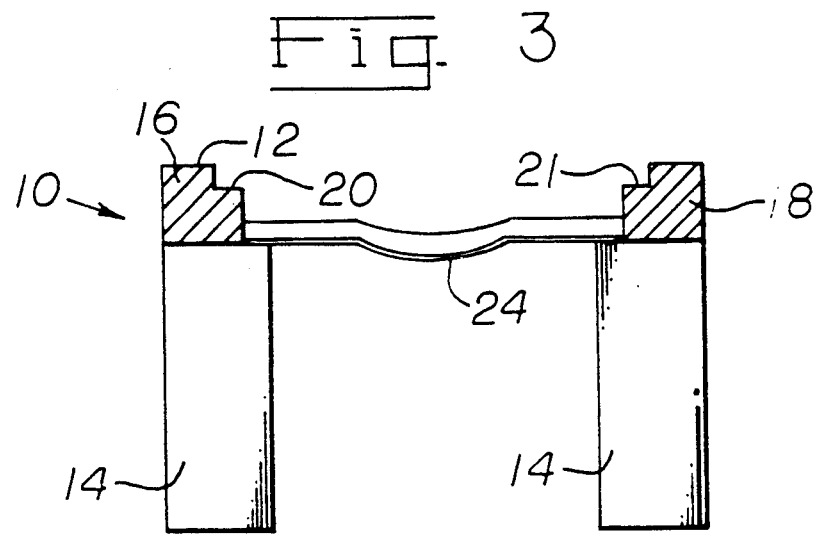

United States Patent [19]

Coates

[11] Patent Number: 5,035,699
[45] Date of Patent: Jul. 30, 1991

[54] PATELLA TRACK CUTTER AND GUIDE

[75] Inventor: Bradley J. Coates, Cordova, Tenn.

[73] Assignee: Dow Corning Wright, Arlington, Tenn.

[21] Appl. No.: 462,268

[22] Filed: Jan. 9, 1990

[51] Int. Cl.5 .............................................. A61F 5/04
[52] U.S. Cl. ........................................ 606/86; 606/87
[58] Field of Search ...................... 606/53, 79, 86, 82, 606/83, 81, 84, 85, 87, 88, 89; 623/18, 23

[56] References Cited

U.S. PATENT DOCUMENTS

| 930,477 | 8/1909 | Hudson | 606/80 |
|---|---|---|---|
| 3,412,733 | 11/1968 | Ross | 606/81 |
| 3,633,583 | 1/1972 | Fishbein | 606/81 |
| 3,667,456 | 6/1972 | Charnley | 606/81 |
| 4,004,581 | 1/1977 | Heinke | 606/81 |
| 4,179,810 | 12/1979 | Kirsch | 606/82 |
| 4,467,801 | 8/1984 | Whiteside | 606/88 |
| 4,721,104 | 1/1988 | Kaufman et al. | 606/88 |
| 4,730,616 | 3/1988 | Frisbie | 606/87 |
| 4,856,503 | 8/1989 | Schelhas | 606/80 |
| 4,926,847 | 5/1990 | Luckman | 606/88 |

Primary Examiner—Robert A. Hafer
Assistant Examiner—Michael Brown
Attorney, Agent, or Firm—John L. Chiatalas

[57] ABSTRACT

A surgical device for accurately positioning and cutting a patellar groove in a resected distal femur to receive a patellar track portion of a prosthesis, including a guide element adapted to fit over the distal end of a resected femur, having a central opening which exposes the central, distal an anterior aspects of the femur, each side of the opening being provided with a track, extending the length of the patella track, and, a cutting tool having a cutting surface, perferably convex, adapted to fit into the central opening for the purpose of cutting or abrading a groove into the femur as the tool is moved along the opening. The tool, which is preferably a rotary cutter provided with independently rotatable track-engaging surfaces on each side of the opening is adapted to engage and move along the track.

10 Claims, 4 Drawing Sheets

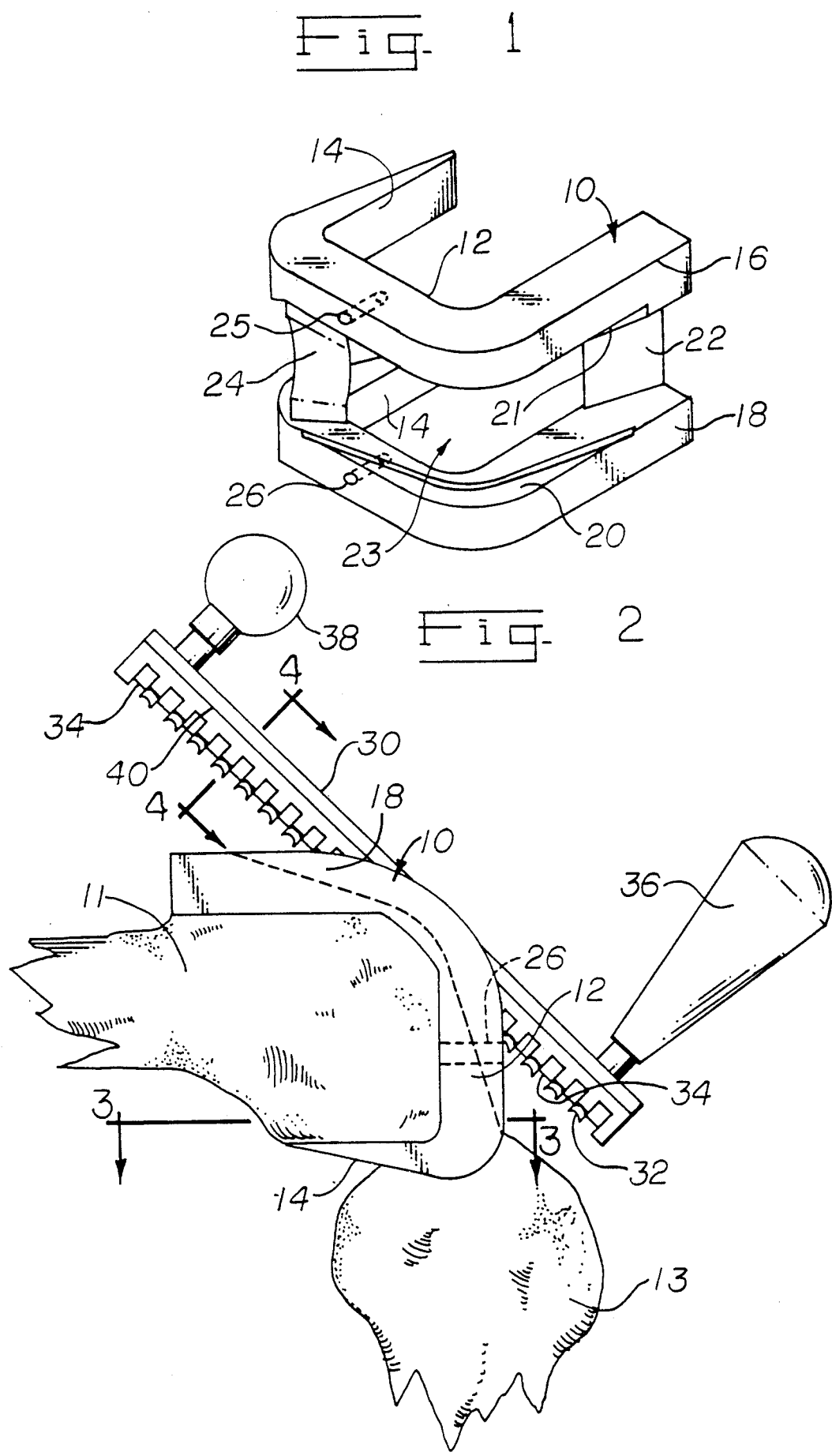

PATELLA TRACK CUTTER AND GUIDE

This invention relates to surgical device for use by orthopedic surgeons useful in the implantation of distal femoral knee prostheses, particularly in cases where a patellar prosthesis is implanted.

Surgical instruments for various bone shaping or resection operations required for implantation of prosthetic devices have been devised to assist orthopedic surgeons in accurately performing the necessary cutting steps. One example is the apparatus described in Kaufman and Whiteside U.S. Pat. No. 4,721,104. In that patent a femoral shaping apparatus is described which employs a template having a straight slot therein for cutting a relatively deep recess for an intercondylar stabilizing housing of a knee implant. The patent, however, does not disclose a cutting guide having a curved track useful for forming a groove to accommodate a patellar track on such a prosthesis.

Heretofore it has been common practice for a surgeon to form a patellar track groove in a resected distal femur, if required, due to the nature of the particular knee prosthesis being implanted, by use of various cutting or abrading tools or instruments without aid of any type of locating or guiding instrument. In design and seating of a prosthesis it is important to retain the original patella/femoral joint line to avoid placing undue stress on the patella and its connective tissues. A need has existed for an improved system for accurate placement and cutting of a groove to accomodate a patellar track portion of a prosthesis to insure accurate seating of the prosthesis for long term wear and stability of a patellar prosthesis. The present invention relates to a device intended to fill this need.

More particularly, the invention relates to a surgical device for accurately positioning and cutting a patellar groove in a resected distal femur including in combination a generally U-shaped guide element which is adapted to fit over the distal end of a resected femur and over the anterior and posterior surfaces thereof, and a cutting tool adapted to move along an elongated continuous central opening in the guide element to cut an indentation to receive a patellar track along the central distal and anterior aspects of the resected femur. The anterior and distal surfaces of the guide element are provided with a pair of curved parallel tracks, one on each side of the central opening. The tracks extend at least the length of the patella groove to be cut and provide means to guide a cutting tool. Such a cutting tool may either be hand operated or may be of a rotary or other power driven type. The present invention, in a further embodiment, provides an improved rotary cutting tool for use in conjunction with a guide element. In any event, such a cutting tool is provided with a cutting surface, usually convex shaped, adapted to fit into the central opening of the guide for the purpose of cutting or abrading a patella groove into said femur. Such a tool is also provided with a track-engaging surfaces spaced apart to span the opening. Each of the track engaging surfaces is adapted to engage and move along one of said tracks, thus allowing the cutting tool to be guided accurately along the desired portion of the resected femur. An important advantage of the invention resides in the ability to accurately control the depth of the patellar track channel.

Figure 4:
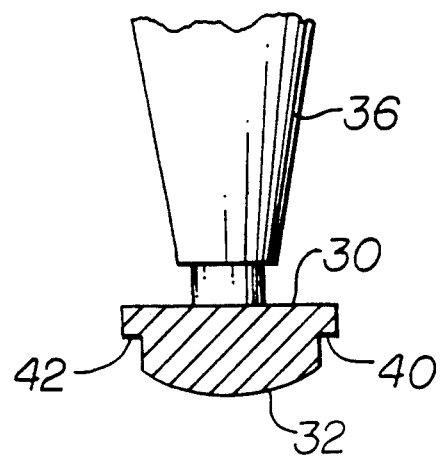
Figure 5:
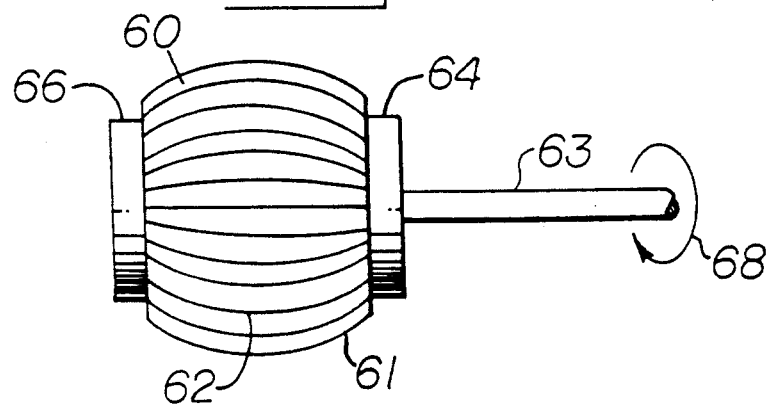
Figure 6:
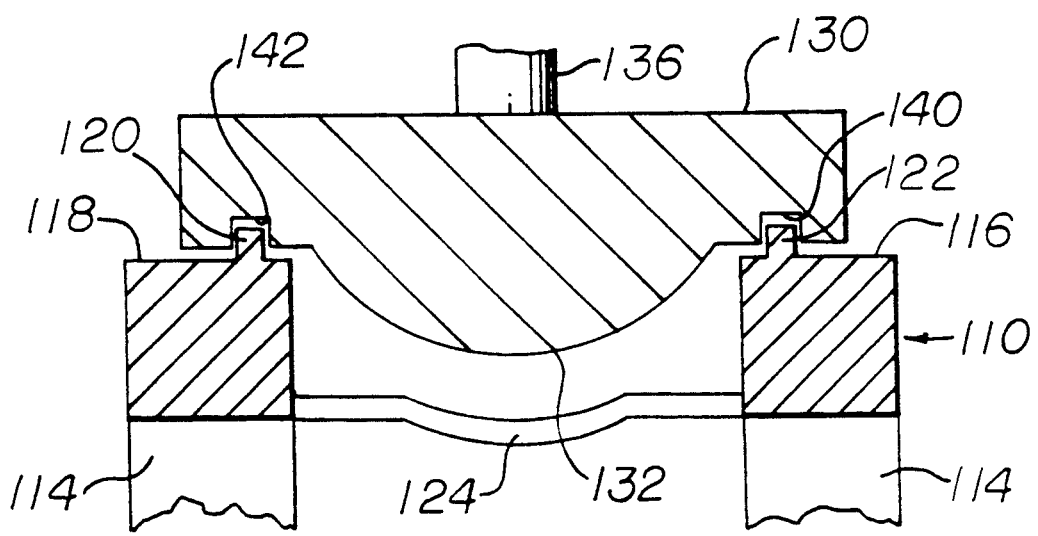
Figure 7:
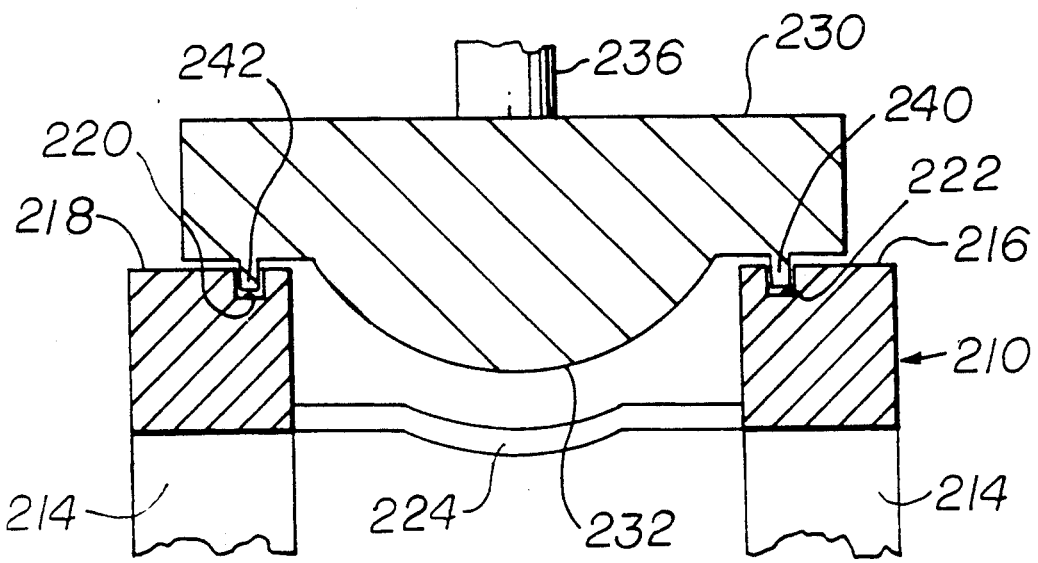
Figure 8:
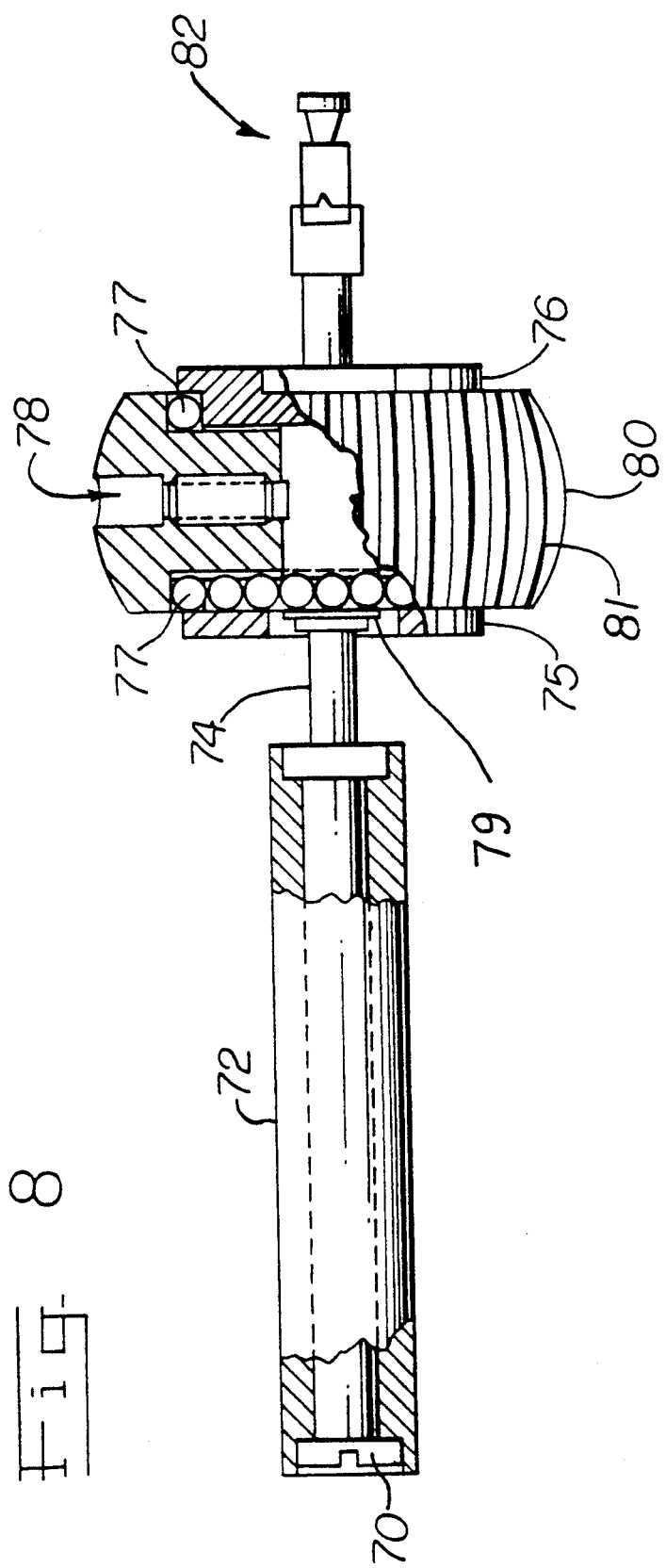

The invention will be further explained with reference to the following detailed description and drawings wherein:

FIG. 1 is a perspective view of a cutting guide of this invention adapted to fit over the distal end of a resected femur, FIG. 2 is a side view illustrating the use of the guide of this invention in place on a femur in conjunction with a cutting tool, FIG. 3 is a cross-sectional view of cutting guide 10 of FIG. 1 taken along line 3—3 of FIG. 2, FIG. 4 is a cross-sectional view of the cutting tool shown in FIG. 2 taken along line 4—4, FIG. 5 is a side view of an alternative cutting tool which may be power driven that may be employed in conjunction with the cutting guide of this invention, FIG. 6 is a cross-sectional view of a further embodiment of the invention taken along a cross-section similar to that of FIG. 3, FIG. 7 is a cross-sectional view of a still further embodiment of the invention also taken along a cross-section similar to that of FIG. 3, and, FIG. 8 is a side view of a further embodiment of a power driven rotary cutter for use in combination with a guide according to the invention, with parts shown in cross-section.

Referring more particularly to the drawings, there is seen in FIG. 1 a cutting guide element 10 of generally U-shaped configuration having a section 12 adapted to fit over the distal end of a resected femur 11 as shown in FIG. 2. End 14 is adapted to fit on the posterior side of the resected femur and consists of 2 arms adapted to fit over the medial and lateral condyles of the femur. The anterior side of the cutting guide device consists of ends 16 and 18 which are a continuation of the distal surface contacting portion 12 and are adapted to closely fit over the anterior side of the resected femur as indicated in FIG. 2. Channels 20 and 21 are cut or sunk into the central edges of portion 16 and 18 of the device to form a curved track in which the cutting device can be moved during the course of cutting procedures. The central portion of the cutting guide 10 consists of an elongated opening 23 which exposes at least the distal and anterior aspects of the resected femur so that a patellar groove may be cut therein. Connecting members 22 and 24 serve to connect the device together into an integral structure. The distal surfaces of the connecting members may also be curved as illustrated with element 24 to provide room for the cutting tool during use.

Holes 25 and 26 are preferably formed in the distal surface portion of the guide member in order to provide a means for securing the guide to the resected femur. These holes can be used to accurately drill holes into the femur for the purpose of installing anchoring pins to fix the guide to the femur. These holes are preferably positioned so that they will receive anchoring pegs on the actual implant.

As best seen in FIG. 2 a hand-operated cutting tool 30 may be employed in conjunction with cutting guide 10. Tool 30 is provided with a generally convex-shaped cutting portion 32, the cross-section of which is seen in FIG. 4. A series of cutting teeth 34 are positioned along the length of cutting surface 32. The edges of surface 32 are provided with ledges 40 and 42 along the entire length thereof. Ledges 40 and 42 act as track-engaging means so that the cutting tool 10 can be moved along a desired central course to cause resection of a patellar channel in the distal and anterior surfaces of femur 11. With the embodiment of FIG. 2, the surgeon can by hand reciprocate cutting tool 30 in guide 10 using handles 36 and 38.

In the embodiment of FIG. 5, an alternative cutting tool 60 is employed which is provided with an annular convex-shaped cutting surface 61. Surface 61 is provided with a series of cutting teeth 62 around the circumference thereof for purposes of resection of femur 11. Shoulders 64 and 66 are provided on opposite ends of the cutting surface so that the cutting tool 60 can be moved along cutting guide tracks 20 and 21. Shaft 63 is provided so that tool 60 can be driven by a conventional rotary power tool (not shown) so that it rotates as indicated by arrow 68.

FIGS. 6 and 7 represent alternative embodiments of track configurations with appropriately modified track engaging surfaces on the cutting tool. Firstly, in FIG. 6 there is seen a modified cutting guide element 110 having anterior arms 114 and distal elements 116 and 118, the surfaces of which, adjoining the central opening therebetween, are provided with raised rail track members 120 and 122. As also seen in FIG. 6, the cutter 130 is provided with track engaging grooves 140 and 142 which are adapted to engage the raised rail track elements and guide cutter 130 in an appropriate path to form a resected patellar groove.

FIG. 7 shows in analogous fashion a revised embodiment in which channels 220 and 222 form the track means in the distal surfaces 216 and 218 of guide element 210. In this configuration, the track engaging portions 240 and 242 of cutting tool 230 comprised track engaging projections on the flanges provided on each side of the cutting surface 232. In other respects, the embodiments of FIGS. 6 and 7 have other components analogous to those shown in FIGS. 1 through 5.

FIG. 8 shows a preferred embodiment of a rotary cutter for use in connection with the combination of the present invention. In that embodiment that cutting element is power driven while the track engaging surfaces are free to rotate separately therefrom. A handle 72 is rotatably affixed to one end of power driven shaft 74, for example, by a screw 70. Handle 72 may be formed from polytetrafluoroethylene or other low friction materials. A cutter 80 provided with cutting teeth 81 is affixed to shaft 74 by means of set screw 78. On each side of the cutting element 80 is an indentation or race 77 containing ball bearings which allow guide track engaging discs 75 and 76 to rotate separately from shaft 74. Appropriate mechanical connectors such as snap ring 79, which may fit into a groove on shaft 74, are utilized to hold the cutter in position on the shaft. The power drive end shaft 74 is provided with an appropriate connector to permit attachment to a rotary power driving device. For example, end 82 may be a "Hudson (R)" end which attaches to a power reamer drive.

The ball bearings as shown in races 77 may be replaced, for example, by polytetrafluoroethylene washers or other low friction washers such as ultra high molecular weight polyethylene or nylon or the like.

It has been found that due to the fact that washers 75 and 76 are free wheeling from power shaft 74, the cutter 80 will not jump out of the track if the shaft is inadvertently twisted. Forcible pulling of the cutter along the track and excessive wear of the track is also obviated by this preferred embodiment.

In practicing the present invention, a surgeon would follow normal procedures for resection of the distal femur which would be resected to a size adapted to fit the dimensions of the particular guide unit 10 being employed. In general, the surgeon can observe a remaining part of the original patellar track between the resected condyles and can center the guide element 10 on such track. In the event that the track is not sufficiently observable after resection, the surgeon would center the guide 10 on the posterior condyles themselves. The guide element 10 would generally be provided to the surgeon in a number of separate sizes which would match the corresponding implant sizes provided to the surgeon. Resection of a groove by the cutting tool to the depth permitted by the guide will ensure a proper depth and placement of the newly formed patellar track. While a number of embodiments of the invention have been disclosed herein, further revisions and alternative embodiments falling within the scope and spirit of the appendant claims will be apparent to those skilled in the art.

What is claimed is:

1. A surgical device for accurately positioning and cutting a patellar groove in a resected distal femur for the implantation of a femoral prosthesis, said device comprising in combination:

a generally U-shaped guide having anterior and distal surfaces, adapted to fit over anterior, posterior and distal surfaces of the resected femur, including an elongated continuous central opening in the guide which is adapted to expose the central, distal and anterior resected aspects of the femur, the opening comprising lateral sides which define a pair of parallel curved tracks extending therealong the desired length of the patellar groove; and a patella cutting tool having a track-engaging surface adapted to travel along the curved tracks and a cutting surface adapted to fit into the central opening for cutting or abrading the patellar groove into the exposed distal femur as the tool travels along the tracks.

2. The device of claim 1 wherein the tracks comprise elongated channels cut into the sides of the central opening.

3. The device of claim 2 wherein the channels comprise ledges extending along the sides of the central opening.

4. The device of claim 1 wherein the tracks comprise raised rails extending along the surfaces of the guide member adjacent the central opening.

5. The device of claim 1 wherein the cutting tool comprises a hand-operated planer.

6. The device of claim 1 wherein the cutting tool comprises a power-driven rotary cutter.

7. The device of claim 6 wherein the cutter comprises an annular-shaped cutting head secured to power-driven rotary shaft, the track-engaging surfaces further comprising disc-shaped members on opposed sides of the cutting head which are freely rotatable on the shaft.

8. The device of claim 7 further comprising a race of ball bearings positioned between each of the disc-shaped members and the cutting head.

9. The device of claim 1 wherein the cutting tool is convex.

10. The device of claim 1 wherein the distal surface of the guide member on each of the sides of the opening is provided with an aperture suited for attachment of the guide member to the surface of the resected distal femur bone by means of fasteners, the apertures being positioned to coincide with the location of attachment pegs provided on the femoral prosthesis.

* * * * *